United States Patent [19]

Buser et al.

[11] Patent Number: 4,879,413

[45] Date of Patent: Nov. 7, 1989

[54] PROCESS FOR THE PREPARATION OF A SOLID ADDUCT OF SULFURIC ACID AND UREA

[75] Inventors: Hansjörg Buser, Marly; Adolf Morand, Villars-sur-Glane, both of Switzerland

[73] Assignee: Ciba-Geigy AG, Basel, Switzerland

[21] Appl. No.: 244,632

[22] Filed: Sep. 12, 1988

Related U.S. Application Data

[60] Continuation of Ser. No. 921,848, Oct. 23, 1986, abandoned, which is a continuation of Ser. No. 420,535, Sep. 20, 1982, abandoned, which is a division of Ser. No. 235,388, Feb. 17, 1981, Pat. No. 4,366,232.

[30] Foreign Application Priority Data

Feb. 22, 1980 [CH] Switzerland ........................ 1435/80

[51] Int. Cl.⁴ ........................................... C07C 127/01

[52] U.S. Cl. ........................................ 564/63; 564/32; 564/73

[58] Field of Search .............................. 564/32, 63, 73

[56] References Cited

U.S. PATENT DOCUMENTS 4,116,664 9/1978 Jones ................................ 564/63 X 4,310,343 1/1982 Verdegaal et al. ............... 564/63 X

FOREIGN PATENT DOCUMENTS 1109619 4/1968 United Kingdom .

OTHER PUBLICATIONS

Nurekhmetov et al., CA 78:97098j (1973).

Molodkin et al., CA 69:43305d (1967).

*Primary Examiner*—Charles F. Warren

*Assistant Examiner*—Carolyn S. Greason

*Attorney, Agent, or Firm*—Wenderoth, Lind & Ponack

[57] ABSTRACT

A method for processing exposed and developed photographic silver dye-bleach materials, in which the exposed and developed material is treated with aqueous bleaching preparations which contain (a) an acid component, (b) a silver complexing agent, (c) one or more bleach catalysts, (d) optionally an antioxidant, (e) optionally a water-soluble oxidizing agent and (f) optionally a bleaching accelerator.

A water-soluble and as a rule solid adduct of an acid amide or a lactam and a strong mineral acid is used as acid component (a).

4 Claims, No Drawings

PROCESS FOR THE PREPARATION OF A SOLID ADDUCT OF SULFURIC ACID AND UREA

This application is a continuation of now abandoned application Ser. No. 921,848, filed Oct. 23, 1986, which application is a continuation of now abandoned application Ser. No. 420,535, Sept. 20, 1982, which application is a division of application Ser. No. 235,388, filed Feb. 17, 1981 (now U.S. Pat. No. 4,366,232.

The present invention relates to a novel method for processing exposed and developed silver dye-bleach materials and to preparations which are suitable for this method and are in the form of ready-for-use aqueous solutions or of concentrates in liquid or solid form which can be diluted with water.

In general, four process steps are required for the processing of silver dye-bleach materials:

(A) Developing of the latent silver image, (B) dye bleaching at the image areas containing metallic silver, (C) silver bleaching: conversion of the residual silver image to silver compounds which are soluble as complexes and (D) fixing: dissolving ou and removing all of the silver compounds which are soluble in the form of complexes.

Several methods have been disclosed which make it possible to shorten this process sequence: in German Offenlegungsschrift No. 2,448,433, for example, a method is described in which steps (B) dye bleaching and (C) silver bleaching are combined in a single step. A processing sequence in which steps (C) silver bleaching and (D) fixing are carried out at the same time in a single bleach-fixing bath has been described in U.S. Patent Specification No. 3,868,253. Finally, German Patent Specification No. 735,672 discloses a method for processing silver dye-bleach materials, in which process steps (B), (C) and (D) are carried out at the same time in a single bath.

The preparations (baths) used for dye bleaching and/or silver bleaching or the combined bleach-fixing are strongly acid, i.e. have a pH value of below 2 and in particular of below 1. As a rule, the pH is adjusted to this value using strong acids, in particular mineral acids, such as hydrochloric acid, sulfuric acid, nitric acid or phosphoric acid, or also sulfamic acid. Good results are also obtained with certain strong organic acids, such as p-toluenesulfonic acid.

The mineral acids most frequently used hitherto for the bleaching baths have several important disadvantages which can have adverse consequences for general use. Thus, for example, hydrochloric acid is highly volatile and therefore has a particularly corrosive action on, for example, apparatus and equipment in which processing of the photographic material is carried out. Moreover, most mineral acids, with the exception of sulfamic acid, are liquid. Their use, especially by amateurs, can therefore involve certain hazards, for example as a result of spillage or breakage of vessels.

For this reason, the use of solid acids in place of liquid acids is particularly advantageous. It facilitates the making-up, the transport and the storage of preparations for dye bleaching and/or silver bleaching. Sulfamic acid, which in itself is suitable and which can easily be prepared in a free-flowing powder form, can in many cases be used as a replacement for liquid mineral acids. However, its relatively poor solubility in water is a disadvantage. Moreover, it has been found that it reacts with tertiary phosphines, which are used as bleaching accelerators, and results in unstable bleaching baths. p-Toluenesulfonic acid, which likewise can be employed in a free-flowing powder form, possesses high solubility in water and gives stable bleaching baths. A disadvantage is its price, which is considerably higher than that of mineral acids, and also the high molecular weight, which makes it necessary to employ large amounts by weight. The high carbon ballast of p-toluenesulfonic acid also has unfavourable consequences from the ecological standpoint, because of the high oxygen demand in the effluents.

The object of the present invention is to provide strong mineral acids, such as are required for processing photographic silver dye-bleach materials, in a suitable form in order thus to overcome the disadvantages mentioned above.

It has now been found that adducts of mineral acids with certain acid amides and lactams can be used in place of mineral acids in bleaching baths for the silver dye-bleach process. A number of these adducts are solid and have good stability and high solubility in water. In aqueous solution, they readily dissociate into their original constituents, so that in many cases it is possible to employ such solutions in place of the corresponding mineral acids.

The present invention relates to a method for processing exposed and developed photographic silver dye-bleach materials, by treating the exposed and developed material with aqueous bleaching preparations which contain (a) an acid component, (b) a silver-complexing agent, (c) one or more bleach catalysts, (d) optionally an antioxidant, (e) optionally a water-soluble oxidising agent and (f) optionally a bleaching accelerator, wherein (a) is a water-soluble adduct of an acid amide or a lactam and a strong mineral acid.

The invention also relates to the preparations for carrying out the method and to the concentrates or partial concentrates for preparing the ready-for-use aqueous preparations, and the use of adducts of acid amides or lactams and strong mineral acids in aqueous preparations for silver bleaching and/or dye bleaching, and also to a process for the preparation of urea-sulfuric acid adducts.

The acid amides used to prepare the adducts with the strong mineral acids are those of low-molecular aliphatic acids, for example having 1 to 4 and in particular 1 or 2 carbon atoms, and also of monocyclic aromatic acids, such as, in particular, of benzoic acids, which can be substituted by alkyl($C_1$–$C_4$), halogen, nitro or cyano, and also the diamides (ureas) of carbonic acid and thiocarbonic acid. The nitrogen atoms of the amides can be monosubstituted or in particular disubstituted by alkyl having 1 to 4 carbon atoms, especially by methyl. Examples of suitable amides are thiourea, benzamide and, preferably, urea, formamide, dimethylformamide, acetamide and dimethylacetamide.

Suitable lactams (cyclic amides) are those of $\gamma$, $\delta$- and $\epsilon$-aminoacids (4 to 6 carbon atoms) which can, if desired, be substituted on the nitrogen atom by lower alkyl($C_1$–$C_4$), especially by methyl. Examples of the said lactams are piperidone ($\delta$-valerolactam) and also, in particular, 2-pyrrolidone ($\gamma$-butyrolactam), N-methyl-2-pyrrolidone and caprolactam.

Suitable strong mineral acids are phosphoric acid and perchloric acid and also, in particular, sulfuric acid, hydrochloric acid or other hydrogen halide acids (HBr, HI) and nitric acid.

A review of the properties of acid amide-mineral acid adducts is given, for example, in J. Zabicky (editor) "The Chemistry of Amides" from the series "The Chemistry of Functional Groups", Interscience, London 1970.

Table 1, which is given below, shows a summary of the properties of diverse adducts of mineral acids with amides and lactams. Some of the adducts, which in general are colourless and stable, are liquid and others occur in crystalline form. As far as possible, the melting points of crystalline products are given. Some of the compounds are hygroscopic. Table 1: Properties of diverse adducts of mineral acids with amides and lactams

TABLE 1

Properties of diverse adducts of mineral acids with amides and lactams Melting point (±5°)

| Amide/lactam | Acid $H_2SO_4$ | $\frac{1}{2}H_2SO_4$ | HCl | $HNO_3$ | $HClO_4$ | $H_3PO_4$ |
|---|---|---|---|---|---|---|
| Urea | 70 | 80 | 40 | 150 | 30 | 110 |
| Tetramethylurea | — | — | — | — | N | N |
| Formamide | 50 | — | + | — | + | — |
| Dimethylformamide | — | — | 40 | — | — | — |
| Acetamide | 40 | — | 130 | 150 | 30 | — |
| N,N—Dimethyl-acetamide | 60 | 40 | 120 | — | N | N |
| 2-Pyrrolidone | + | — | 130 | — | + | — |
| N—Methyl-2-pyrrol-idone | 60 | — | 80 | — | — | — |
| Caprolactam | — | — | 150 | — | — | — |
| Benzamide | + | + | 80 | — | N | N |
| Thiourea | 80 | — | 110 | 140 | 100 | — |

+ Crystalline product, but melting point cannot be determined because the adduct is too hygroscopic or decomposes before the melting point is reached
— no solid product
N no result Particularly well known adducts are those of mineral acids with urea, in particular the adducts of one mol of urea with 0.5 or 1 mol of sulfuric acid. Data on the properties of these adducts, on their stability and on the reaction kinetics in the melt and in aqueous solutions are given, inter alia, in L. H. Dalman, J. Am. Chem. Soc., 56, 549 (1934), P. Baumgarten, Chem. Ber., 69, 1929 (1936), E. Cherbuliez & F. Landolt, Helv., 29, 1438 (1946) and G. M. Schwab and E. Schwab-Agallidis, Angew. Chemie, 65, 418 (1953).

Adducts of mineral acids with urea are prepared either direct from the components or their solutions or by the action of mineral acids on cyanamide, in which case the latter decomposes to give urea, which then enters into the adduct with the acid.

Details of the preparation of urea-mineral acid adducts are to be found, inter alia, in German Patent Specification No. 239,309, in U.S. Patent Specification No. 3,330,864 or in British Patent Specifications Nos. 196,601 and 1,109,619.

The adducts used according to the invention are very stable in the solid form and can easily be prepared in the form of free-flowing, water-soluble powders or granules. Preferred adducts are those of urea with sulfuric acid or nitric acid, and also of thiourea with sulfuric acid and of acetamide with hydrochloric acid.

The adducts of urea with sulfuric acid, which are particularly suitable as the acid component for the preparations according to the present invention, exist in two stable forms: urea-sulfate, i.e. the adduct of two mols of urea with one mol of sulfuric acid, and ureahydrogen sulfate, i.e. the adduct of one mol of urea with one mol of sulfuric acid. Both forms can be prepared direct, in an anhydrous, solid form, by a simple process of preparation:

According to this process, urea is introduced direct, in solid form, into 100 per cent sulfuric acid (monohydrate), with cooling, the temperature not being allowed to rise above 100° C. (preferably 70° C. to 100° C.) during the reaction. In this way, a melt of urea-hydrogen sulfate or of urea-sulfate, depending on whether one or two mols of urea were introduced per mol of sulfuric acid, is obtained direct. The compounds are converted to the solid form by cooling and optionally comminuted.

It is essential that a precisely 100 per cent sulfuric acid is used when preparing the said ureasulfuric acid adducts; if the melt contains free water or sulfur trioxide, the stability of the melt is distinctly reduced. The melt can be converted to a solid form, which is suitable for use, by suitable processes, such as are used, for example, in the preparation of alkali metal hydroxides (cf. Ullmanns Encyclopadie der technischen Chemie (Encyclopaedia of Industrial Chemistry), 4th edition, Verlag Chemie, Weinheim, Volume 17 (1979), page 204 et seq.). In particular, it can be crystallised in the form of free-flowing beads, pills, flocks or flakes which are immediately soluble in water. The sulfuric acid adducts can be brought into the form of beads if they are sprayed, for example, in a cooling tower.

It is also possible to prepare the sulfuric acid adducts of urea in an aqueous medium. With this method, urea is introduced at about 50° C. into an aqueous sulfuric acid solution, with stirring. This gives a suspension of the urea-sulfate, which crystallises out and is filtered off and, if desired, dried (cf. Ullmanns Encyclopadie der technischen Chemie (Ullmann's Encyclopaedia of Industrial Chemistry), 4th edition, Verlag Chemie, Weinheim, Vol. 2 (1972), pages 154, 672, 698.

Furthermore, solid, hygroscopic acids can be brought into a less hygroscopic form by forming an adduct with amides. For example, trichloroacetic acid and p-toluenesulfonic acid liquefy completely when they are exposed to an atmosphere of 76% relative humidity. However, the adducts of these acids with, for example, urea, pyrrolidone or thiourea remain in crystalline form under the said conditions.

The baths used for dye bleaching contain, as the most important constituents, a strong acid in the form of the acid adduct (a), a complexing agent for the silver (b) and a dye-bleach catalyst (c). The dye-bleach catalysts used are, in particular, diazine compounds, such as pyrazine, quinoxaline or phenazine and their derivatives.

Suitable bleach catalysts have been disclosed, for example, in German Patent Specifications and Patent Publications Nos. 735,672, 1,547,720, 2,144,297, 2,144,298, 2,722,776 or 2,722,777.

A suitable silver-complexing agent can be, for example, thiourea. Advantageous results are obtained when a water-soluble iodide (alkali metal iodides, preferably sodium iodide or potassium iodide, or also ammonium iodide) is used as the complexing agent, as is described, for example, in U.S. Pat. Specification No. 3,620,744. Enrichment of interfering silver complexes in the bleaching bath can be prevented in this way. However, an antioxidant, which prevents oxidation of the iodide to iodine, must also be used.

Advantageously, reductones or water-soluble mercapto compounds are used as the antioxidant (d).

Suitable reductones are, in particular, acireductones containing a $\beta$-carbonyl-1,2-enediol grouping, such as reductine, triose-reductone or preferably ascorbic acid. Suitable mercapto compounds are, for example, thioglycerol, but especially the compounds of the formula (1) $HS\text{-}C_qH_{2q}\text{-}B$ or preferably (2) $HS\text{-}(CH_2)_m\text{-}COOH$ in which q is an integer with a value of from 2 to 12, B is a sulfonic acid group or carboxylic acid group and m is one of the numbers 3 and 4. Mercapto compounds which can be used as antioxidants are described in German Offenlegungsschrift No. 2,258,070 and in German Offenlegungsschrift No. 2,423,814. Compounds suitable as further antioxidants are alkali metal, alkaline earth metal or ammonium bisulfate adducts of organic carbonyl compounds, preferably alkali metal or ammonium bisulfite adducts of monoaldehydes having 1 to 4 carbon atoms or of dialdehydes having 2 to 5 carbon atoms (German Offenlegungsschrift 2,737,142).

Examples are the particularly preferred formaldehyde-bisulfite adduct and also the corresponding adducts of acetaldehyde, propionaldehyde, butyraldehyde or isobutyraldehyde and of glyoxal, malonaldehyde, or glutaraldehyde. If desired, the tertiary, water-soluble phosphines named below as bleaching accelerators can also be used at the same time as antioxidants.

In the case of baths with which it is intended to bleach the dye and the image silver at the same time, or also in the case of baths which are used only for silver bleaching, it is necessary to add a water-soluble oxidising agent (e); in addition, the concentration of the dye-bleach catalysts must be considerably increased compared with that in a simple dye-bleach bath, as has been described, for example, in German Offenlegungsschrift No. 2,448,433.

The oxidising agents (e) used are advantageously water-soluble aromatic mononitro and dinitro compounds, as well as anthraquinonesulfonic acid derivatives. The use of such oxidising agents serves to influence the colour balance and the contrast in the images produced by the dye-bleach process and has been disclosed in German Patent Specification No. 735,672, British Patent Specifications Nos. 539,190 and 539,509 and Japanese Patent Publication No. 22,673/69.

The mononitro and dinitro compounds are preferably mono- or di-nitrobenzenesulfonic acids, for example those of the formula

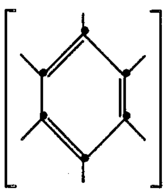

(3)

$(-NO_2)_n-R-R'(-H)_{3-n}-SO_3H$ in which n is 1 or 2 and R and R' are hydrogen, lower alkyl having 1 to 4 carbon atoms, hydroxyl, alkoxy, amino or halogen (chlorine or bromine). The sulfonic acids can be added in the form of readily soluble salts. Suitable compounds are, for example, the sodium or potassium salts of the following acids: o-nitrobenzenesulfonic acid, m-nitrobenzenesulfonic acid, 2,4-dinitrobenzenesulfonic acid, 3,5-dinitrobenzenesulfonic acid, 3-nitro-4-chlorobenzenesulfonic acid, 2-chloro-nitrobenzenesulfonic acid, 4-methyl-3,5-dinitrobensenesulfonic acid, 3-chloro-2,5-dinitrobenzenesulfonic acid, 2-amineo-4-nitrobensenesulfonic acid, 2-amino-4-nitro-5-methoxybenzenesulfonic acid and 4-nitrophenol-2-sulfonic acid.

As well as acting as silver-bleaching agents, the compounds of component (e) serve to level off the grauation.

Suitable bleaching accelerators (f) are, for example, quaternary ammonium salts, such as have been disclosed in German Offenlegungsschriften Nos. 2,139,401 and 2,716,135. They are preferably quaternary, substituted or unsubstituted piperidine, piperazine, pyrazine, quinoline or pyridine compounds, the latter being preferred. Furthermore, tetraalkylammonium compounds (alkyl having 1 to 4 carbon atoms) and alkylenediammonium compounds (alkylene having 2 to 6 carbon atoms) can also be used. Specific compounds are: tetraethylammonium iodide: $(CH_3)_3N^{\oplus}(CH_2)_2N^{\oplus}(CH_3)_3 0.2I^{\ominus}$; $(CH_3)_3N^{\oplus}(CH_2)_6N^{\oplus}(CH_3)_3 0.2I^{\ominus}$; N-methylpyridinium iodide; N-methylquinolinium iodide; N-hydroxyethylpyridinium chloride; N-hydroxypropylpyridinium bromide; N-methyl-2-hydroxymethylpyridinium iodide; N,N-dimethylpiperidinium iodide; N,N'-dimethylpyrazinium fluorosulfate and $\gamma$-picolinium hydrogen sulfate.

Further bleaching accelerators are the watersoluble tertiary phosphines which are disclosed in German Offenlegungsschrift No. 2,651,969 and which preferably contain at least one cyanoethyl grouping.

They have, for example, the formula

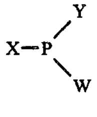

(4)

in which W is $-C_rH_{2r}CN$, $-C_rH_{2r}NO_2$ or a substituted or unsubstituted aryl radical or a heterocyclic radical, r is 1 to 25, X is substituted or unsubstituted alkyl and Y is hydroxyalkyl, alkoxyalkyl, sulfoalkyl, aminoalkyl (alkyl in each case having 1 to 25 and preferably 2 to 4 carbon atoms), phenyl, sulfophenyl or pyridyl. Preferred tertiary phosphines have the formula

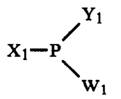

(5)

in which X is $—CH_2CH_2CN$ or $—(CH_2)_2OCH_3$, $Y_1$ is $—(CH_2)_2SO_3^{\ominus}M^{\oplus}$, $—(CH_2)_3—SO_3^{\ominus}M^{\oplus}$, $—(CH_2)_4$-$\ominus SO_3^{\ominus}M^{\oplus}$, $—(CH_2)_2OCH_3$ or $—CH_2N(C_2H_5)_2$, $W_1$ is $—CH_2CH_2CN$ or phenyl and $M^{\oplus}$ is a cation, especially an alkali metal cation, for example the sodium or potassium cation.

Specific compounds are the following: bis-(β-cyanoethyl)-2-sulfoethylphosphine (sodium salt), bis(β-cyanoethyl)-3-sulfopropylphosphine (sodium salt), bis-(β-cyanoethyl)-4-sulfobutylphosphine (sodium salt), bis-(β-cyanoethyl)-2-methoxyethylphosphine, bis-(2-methoxyethyl)-(β-cyanoethyl)-phosphine, (β-cyanoethyl)-phenyl-3-sulfopropylphosphine (sodium salt), (β-cyanoethyl)-phenyl-2-methoxyethylphosphine and bis-(2-methoxyethyl)-phenylphosphine.

It is possible to repeat individual treatments (in each case in a further tank with a bath of the same composition as the preceding bath) and in some cases better utilisation of the bath can be achieved by this means. When the number of available tanks and the schedule permit it is also possible to insert waterbaths between baths of different action. It is left to those skilled in the art to determine, from the sensitometric results, the optimum ratio, depending on the nature of the catalyst selected. All of the baths can contain further conventional additives, for example, hardeners, wetting agents, fluorescent brighteners o UV stablisers.

Baths of conventional composition can be used for silver developing, for example baths which contain hydroquinone as the developer substance and can additionally contain 1-phenyl-3-pyrazolidinone. If desired, a bleach catalyst can already be present in the silver developing bath.

The silver fixing bath can be of known and conventional composition. The fixer used is, for example, sodium thiosulfate or, advantageously, ammonium thiosulfate, if desired with additives such as sodium bisulfite and/or sodium metabisulfite. The fixing bath can also be combined with the bleaching bath, in the form of a so-called bleach-fixing bath.

The aqueous bleaching preparations used as a rule contain components (a) to (f) in the following amounts: (a) acid adduct: 10 to 200 g/l; (b) complexing agent: 2 to 50 g/l and preferably 5 to 25 g/l; (c) at least one bleach catalyst: 0.05 to 10 g/l; (d) optionally an antioxidant: 0.5 to 10 g/l; (e) optionally a water-soluble oxidising agent: 1 to 30 g/l; and (f) optionally a bleaching accelerator: 1 to 5 g/l.

The temperature of the bleaching bath is in general between 20° and 90° C. and preferably between 20° and 60° C. and, or course, the processing time required is shorter at a higher temperature than at a lower temperature. The bleaching baths are stable within the indicated temperature range. In general, the aqueous bleaching preparations required for processing are used in the form of dilute aqueous solutions which contain the sai aqueous bleaching preparations required for processing are used in the form of dilute aqueous solutions which contain the said components. However, other methods are also conceivable, for example use in paste form.

The said temperature range also applies for the other processing steps. The aqueous bleaching preparation according to the present invention can be prepared, for example, from solid or liquid, especially aqueous, concentrates of individual components or of all the components ((a) to (f)). Advantageously, for example, one solid and one liquid concentrate or two liquid concentrates are used, one of which contains the acid adduct (a) and the oxidising agent (e) and the other of which contains the remaining components (b), (c) and, optionally (d) and (f), it being possible to add an additional solvent, such as ethyl alcohol or propyl alcohol, ethylene glycol methyl ether or ethylene glycol ethyl ether, to the latter concentrate in order to improve the solubility, especially of component (c). These concentrates (partial concentrates), which are likewise a subject of the present invention, have excellent stability and can therefore be stored for a prolonged period. Optionally these concentrates can be used after dilution with water or with a mixture of water and an organic solvent.

The concentrates of the individual components or of all the components (a) to (c) and, optionally (d) to (f), or combinations thereof, for example of components (a) and (e) and also of components (b), (d), (c) and (f), can contain, per litre of concentrated preparation, 2 to 20 times and preferably 5 to 10 times the amount of the individual components which have been indicated above for the ready-for-use bleaching bath. The concentrates are as a rule in the form of solid, liquid or paste concentrates.

Thus, for the first time, the possibility exists of using mineral acid-containing bleaching preparations also in the form of solid concentrates, with their known advantages in respect of transport and storage, in place of liquid concentrates.

The present invention also relates to the method for processing exposed and developed silver dye-bleach materials, wherein said method is carried out using aqueous bleaching preparations which contain components (a) to (c) and also, optionally (d) to (f). These bleaching preparations can be dye-bleaching or silver-bleaching baths, combined dye-bleaching and silver-bleaching baths or bleach-fixing baths.

The method according to the invention can be used, for example, in the production of positive coloured images in automatic copying or recording machines or in the rapid processing of other silver dye-bleach materials, for example for scientific recording and industrial purposes, for example coloured photofluorography, and also for the production of coloured negatives and diffusion transfer images.

The base used for the photographic materials to be processed can be a transparent, metallically reflecting or preferably white-opaque material which is not able to absorb any liquid from the baths.

The base can consist, for example, of cellulose triacetate or polyester, which can be pigmented. If it consists of paper fibres, these must be lacquer-coated, or coated with polyethylene, on both sides. The light-sensitive layers are located on at least one side of this base, preferably in the known arrangement, i.e. at the bottom a red-sensitised silver halide emulsion layer, which contains a cyan azo dye, above this a green-sensitised silver halide emulsion layer, which contains a magenta azo dye, and at the top a blue-sensitive silver halide emulsion layer, which contains a yellow azo dye. The material can also contain subbing layers, intermediate layers, filter layers and protective layers, but the total thickness of the layers should as a rule not exceed 20 μ.

The method according to the invention is also particularly suitable for processing exposed silver dye-bleach material which has a special build-up and is suitable, for example, for the production of self-masked images (German Offenlegungsschrift No. 2,547,720).

In the examples which follow, parts and percentages are by weight, unless indicated otherwise.

EXAMPLE 1:

A material, for the silver dye-bleach process, which is suitable for the production of positive reflection copies of a positive original, is prepared in the following manner:

The following layers are applied in the indicated sequence to a white-opaque base:

A red-sensitised layer pair consisting of

1. A red-sensitive gelatin/silver bromide/silver iodide emulsion layer which contains a bleachable cyan azo dye of the formula

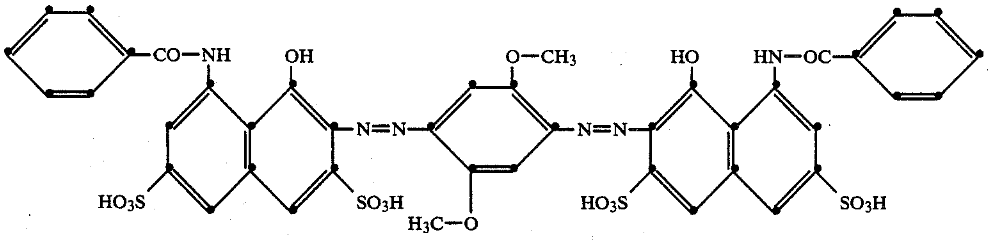

(101)

and has a silver content of 0.144 g of $Ag/m^2$ and
2. a layer consisting of a red-sensitive gelatin/silver bromide/silver iodide emulsion which has a silver content of 0.300 g of $Ag/m^2$ and is free from image dye;
3. a first gelatin interlayer;
4. a green-sensitive gelatin/silver bromide/silver iodide emulsion layer which contains a bleachable magenta azo dye of the formula

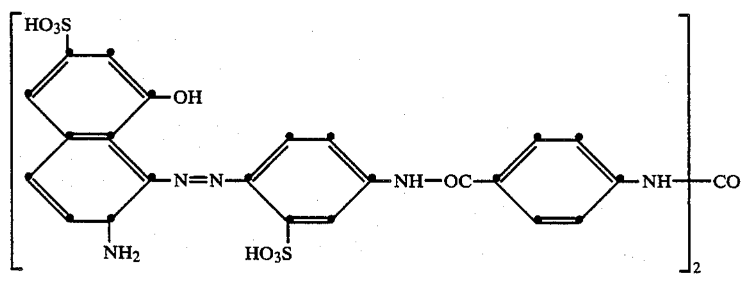

(102)

and has a silver content of 0.212 g of $Ag/m^2$; 5. a layer consisting of a green-sensitive gelatin/silver bromide/silver iodide emulsion which has a silver content of 0.375 g of $Ag/m^2$ and is free from image dye;

6. A second interlayer, consisting of gelatin to which colloidal silver has been added in an amount of 0.007 g of $Ag/m^2$ and an unsensitive silver bromide emulsion which has a silver content of 0.2 g of $AG/m^2$ and has not been spectrally sensitised; a blue-sensitive layer pair consisting of
7. a highly sensitive iodide-free gelatin/silver bromide layer which contains a bleachable yellow azo dye of the formula

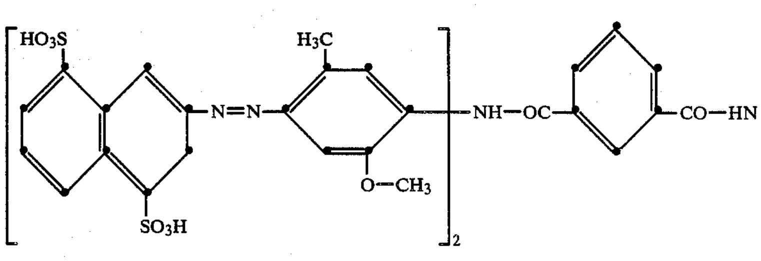

(103)

and has a silver content of 0.360 g of $Ag/m^2$ and 8. a dye-free highly sensitive gelatin/silver bromide/silver iodide layer which has a low iodide content and a silver content of 0.530 g of $Ag/m^2$; and 9. a gelatin protective layer.

The build-up of this material is such that, on processing with a developer which contains a silver ligand, especially sodium thiosulfate, and with the subsequent process steps of dye bleaching and silver bleaching which are necessary for the silver dye-bleach process, the latter steps preferably being combined in a single step, and finally fixing, masking of the blue secondary colour densities of the magenta layer and cyan layer is effected.

A test strip is cut from this photographic material and exposed behind a grey wedge in an additive manner, as follows:

red exposure: 4 seconds
green exposure: 17 seconds
blue exposure: 4 seconds

The following processing solutions were used in the indicated sequence for processing the exposed test strip:

| | |
|---|---|
| 1. Silver developing bath | 2.5 minutes temperature 32° C. |
| Sodium polyphosphate | 1 (g/l) |
| Potassium hydroxide (85%) | 27 (g/l) |
| Boric acid | 21 (g/l) |
| Potassium metabisulfite | 18 (g/l) |
| Anhydrous sodium sulfite | 11 (g/l) |
| 1-Phenyl-3-pyrazolidone | 0.3 (g/l) |
| Hydroquinone | 5 (g/l) |
| Benztriazole | 0.6 (g/l) |
| Potassium bromide | 2 (g/l) |
| Anhydrous sodium thiosulfate | 1.0 (g/l) |
| 2. Washing | 1 minute |
| 3. Bleaching bath | 2.5 minutes |
| Adduct A.-E. (see table given below) | |
| Na salt of m-nitrobenzene sulfonic acid | 7.5 (g/l) |
| Potassium iodide | 5 (g/l) |
| 2,3,6-Trimethylquinoxaline | 1.5 (g/l) |
| Bis-(cyanoethyl)-sulfobutyl-phosphine (Na salt) | 4 (g/l) |

| | Adduct | g/Liter |
|---|---|---|
| A. | $(NH_2)_2CO.H_2SO_4$ | 68 |
| B. | $2[(NH_2)_2CO].H_2SO_4$ | 94 |
| C. | $(NH_2)_2CO.HNO_3$ | 53 |
| D. | $CH_3CONH_2.HCl$ | 41 |
| E. | 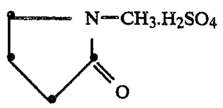 | 43 |
| F. (comparison) | $H_2SO_4$ (96 %) | 44 |

| | |
|---|---|
| 4. Washing | 1 minute |
| 5. Fixing bath | 2.5 minutes |
| Ammonium thiosulfate | 250 g/l |
| Potassium metabisulfite | 50 g/l |
| Potassium hydroxide (85%) | 20 g/l |
| 6. Washing | 3 minutes |
| Total processing time | 12.5 minutes |

After subsequent drying, positive grey wedges are obtained which have a uniform neutral grey colour shade over the entire density range, with $D_{max}$ values of 1.77 (grey) and $D_{min}$ values of 0.03 (grey).

No impairment in the image quality is found when the adducts according to the invention are used in place of the free sulfuric acid customary hitherto.

EXAMPLE 2:

The photographic material used in Examples 2 and 3 given below is identical to that of Example 1 with the exception of the filter layer (6), which this time contains only colloidal silver but no additional non-sensitised emulsion. The processing sequence is similar to that in Example 1 but the silver developing solution does not contain any sodium thiosulfate and therefore no self-masking effect is obtained.

A test strip of the photographic material is exposed in an additive manner, the procedure being similar to that described in Example 1, and the following exposure times are used:

red exposure: 2 seconds
green exposure: 7 seconds
blue exposure: 2 seconds

The following processing solutions are used for the subsequent processing:

| | |
|---|---|
| 1. Silver developing | 3 minutes |
| Na polyphosphate | 1 (g/l) |
| Anhydrous Na sulfite | 40 (g/l) |
| Hydroquinone | 10 (g/l) |
| Na metaborate | 20 (g/l) |
| Na—hydroxide | 3 (g/l) |
| 1-Phenyl-3-pyrazolidone | 1 (g/l) |
| Potassium bromide | 1.5 (g/l) |
| Benztriazole | 0.2 (g/l) |
| Catalyst: | |
| 2,3,6-Trimethylquinoxaline (added in the form of a 1% solution in methylcellosolve) | 0.4 (g/l) |
| 2. Washing | 1 minute |
| 3. Bleaching bath | 3 minutes |
| Pyrrolidone-sulfuric acid adduct (1:1) | 34 g/l |
| 4-Mercaptobutyric acid | 1 ml/l |
| Potassium iodide | 10 g/l |
| Sodium salt of m-nitrobenzene-sulfonic acid | 7 g/l |
| 2,3,6-Trimethylquinoxaline | 2 g/l |
| 4. Washing | 1 minute |
| 5. Fixing bath | 2 minutes |
| Ammonium thiosulfate | 220 g/l |
| Sodium metabisulfite | 10 g/l |
| Sodium sulfite | 40 g/l |
| 6. Washing bath | 4.5 minutes |

The processing temperature was 30° C. during the entire processing.

A second test strip is exposed in the same way and treated in the same processing solutions except that a bleaching bath is used which contains 17 ml of 96% sulfuric acid/litre.

The finished treated and dried test strips give identical sensitometric values, with a $D_{max}$ of, in each case,
1.75 red
1.96 green
2.05 blue
and a $D_{min}$ of, in each case,
0.00 red
0.05 green
0.08 blue (remissive densities).

EXAMPLE 3:

The 9-layer non-masked material used in Example 2 is exposed behind a grey wedge in an additive manner, in the same way as in Example 2, and is then subjected to a processing sequence using four baths, separate baths being used for dye bleaching and silver bleaching, which are carried out consecutively.

The following solutions are used for processing, which throughout is carried out at a temperature of 24° C.:

| | |
|---|---|
| 1. Silver developing | 6 minutes |
| Na polyphosphate | 1 (g/l) |
| Anhydrous Na sulfite | 50 (g/l) |
| Hydroquinone | 5 (g/l) |
| Na metaborate | 15 (g/l) |
| 1-Phenyl-3-pyrazolidone | 0.3 (g/l) |
| Potassium bromide | 3 (g/l) |
| Benztriazole | 0.2 (g/l) |
| 2. Washing | 5 minutes |
| 3. Dye bleaching | 7 minutes |
| Water | 800 ml |
| Urea-nitric acid adduct (1:1) | 32 g |
| Ascorbic acid | 1 g |
| Potassium iodide | 30 g |
| 2,3-Dimethyl-5-amino-6-methoxy-quinoxaline | 0.08 g |
| Water to make up to | 1000 ml |

-continued

| | | |
|---|---|---|
| 4. Washing | 3 | minutes |
| 5. Silver bleaching | 4 | minutes |
| Water | 800 | ml |
| Urea-nitric acid adduct (1:1) | 46 | g |
| Sodium salt of 2,4-dinitro-benzenesulfonic acid | 10 | g |
| Ascorbic acid | | |
| Potassium iodide | 6 | g |
| Ammonium chloride | 20 | g |
| 2,3,6-Trimethylquinoxaline | 0.5 | g |
| Water to make up to | 1000 | ml |
| 6. Washing | 3 | minutes |
| 7. Fixing | 7 | minutes |
| Ammonium thiosulfate | 200 | g/l |
| Anhydrous Na sulfite | 20 | g/l |
| 8. Washing | 8 | minutes |

A second test strip is exposed and processed in an identical manner, except that 14 ml of 96 % sulfuric acid per litre of solution are used in the dyed bleaching solution and 20 ml of 96 % sulfuric acid per litre of solution are used in the silver bleaching solution.

The two positive grey wedges obtained in this way agreed in respect of all sensitometric values. The maximum and minimum densities (remissive densities) measured are:

| | $D_{max}$ | $D_{min}$ |
|---|---|---|
| Red | 1.72 | 0.00 |
| Green | 1.98 | 0.02 |
| Blue | 2.19 | 0.02 |

EXAMPLE 4:

In this example, using the same dyes as in Example 1, a six-layer material is used which contains the cyan dye and the red-sensitised silver halide emulsion assigned thereto in the first layer, a thin interlayer containing pure gelatin as the second layer, the magenta dye with the green-sensitised silver halide emulsion assigned thereto in the third layer, an interlayer consisting of gelatin as the fourth layer, a silver halide layer containing a yellow dye as the 5th layer, and finally a protective layer of pure gelatin as the sixth layer.

A so-called two-bath method consisting of a developing bath and a subsequent combined bath in which dye-bleaching, silver-bleaching and fixing take place virtually at the same time is chosen for processing this material. The bath used as the silver developing bath is identical to that in Example 3; the combined bleaching and fixing bath has the following composition:

| | | |
|---|---|---|
| Thiorea-sulfuric acid adduct (1:1) | 16 | g/l |
| Thiourea | 7 | g/l |
| m-Nitrobenzenesulfonic acid (sodium salt) | 0.8 | g/l |
| 1-Phenyl-2-methyl-6,7-dimethoxy-quinoxaline | 0.5 | g/l |
| Potassium iodide | 3 | g/l |

A second test strip is exposed and processed in an identical manner, except that a combined bleaching and fixing bath is used which contains 9.5 g of 96 % sulfuric acid/l.

The finished processed and dried test strips each give a positive grey wedge and the two wedges have identical sensitometric values. The densities (remissive values) measured are:

| | $D_{max}$ | $D_{min}$ |
|---|---|---|
| Red | 1.75 | 0.05 |
| Green | 1.91 | 0.02 |
| Blue | 1.97 | 0.02 |

EXAMPLE 5:

Concentrate for preparing a combined dye-bleaching and silver-bleaching bath.

A preparation consisting of a solid partial concentrate and a liquid partial concentrate is made up as follows:

| Part I: solid | |
|---|---|
| 92 g | of urea hydrogen sulfate $(NH_2)_2CO \cdot H_2SO_4$ |
| 8 g | of m-nitrobenzenesulfonic acid (sodium salt) |
| 100 g | |
| **Part II: liquid** | |
| 2 g | of 2,3,6-trimethylquinoxaline |
| 6 g | of potassium iodide |
| 2 ml | of 3-mercapto-1,2-propanediol |
| 80 g | of ethylene glycol monomethyl ether |
| 100 ml | made up with water |

Preparation of a combined dye-bleaching and silver-bleaching bath:

| | |
|---|---|
| 100 | parts of solid concentrate I |
| 100 | parts of liquid concentrate II and |
| 800 | parts of water are mixed |
| 1000 | parts |

EXAMPLE 6:

A further preparation comprising a combined dye-bleaching and silver-bleaching bath consists of the following two solid partial concentrates:

| Part III: |
|---|
| 109 g of.diurea sulfate $[(NH_2)_2CO]_2 \cdot H_2SO_4$ |
| 6 g of m-nitrobenzenesulfonic acid (sodium salt) |
| 115 g |
| **Part IV:** |
| 8 g of potassium iodide |
| 1.5 g of 2,3,6-trimethylquinoxaline |
| 4 g of bis-(cyanoethyl)-sulfobutyl-phosphine (sodium salt) |
| 0.5 g of disodium phosphate |
| 14.0 g |

A combined dye-bleaching and silver-bleaching bath is prepared by dissolving parts III and IV in 900 g of water.

What is claimed is:

1. A process for the preparation of an adduct of sulfuric acid and urea, with a urea/sulfuric acid ratio of 2:1 or 1:1, which comprises introducing the solid urea in the indicated ratio into a precisely 100% sulfuric acid (mono-hydrate), the rate at which the urea is introduced and the external cooling being so matched to one another that the temperature is between 70° and 100° C. during the mixing period, and converting the neutral or acid urea-sulfate thus obtained into the solid form by cooling.

2. A process according to claim 1, wherein the melt formed during the reaction is converted into the form of semicircular discrete pills or easily breakable flakes by dripping onto a cooled surface.

3. A process according to claim 1, wherein the melt is converted into the form of beads by spraying in a cooling tower.

4. a process according to claim 1 wherein the solid obtained by cooling is comminuted.

* * * * *